(12) United States Patent
Speck et al.

(10) Patent No.: US 9,618,446 B2
(45) Date of Patent: Apr. 11, 2017

(54) FLUIDIC SPEED OF SOUND MEASUREMENT USING PHOTOACOUSTICS

(71) Applicant: SCHLUMBERGER TECHNOLOGY CORPORATION, Sugar Land, TX (US)

(72) Inventors: Andrew J. Speck, Milton, MA (US); Andrew E. Pomerantz, Lexington, MA (US); Christopher Harrison, Auburndale, MA (US); Oliver C. Mullins, Ridgefield, CT (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 205 days.

(21) Appl. No.: 14/166,623

(22) Filed: Jan. 28, 2014

(65) Prior Publication Data

US 2015/0211984 A1 Jul. 30, 2015

(51) Int. Cl.
*G01N 21/17* (2006.01)
*G02F 1/39* (2006.01)

(52) U.S. Cl.
CPC .......... *G01N 21/1702* (2013.01); *G02F 1/39* (2013.01); *G01N 2201/0697* (2013.01); *G01N 2201/06113* (2013.01)

(58) Field of Classification Search
CPC ....... G01N 21/1702; G01N 2201/0697; G01N 2201/06113

(Continued)

(56) References Cited

U.S. PATENT DOCUMENTS 4,512,197 A * 4/1985 von Gutfeld ...... G01N 29/2418
73/601
5,741,962 A * 4/1998 Birchak .................. E21B 49/10
73/152.16

(Continued)

FOREIGN PATENT DOCUMENTS

WO 2011011512 1/2011
WO 2011146068 11/2011

(Continued)

OTHER PUBLICATIONS

Speck et al., U.S. Appl. No. 14/166,593, filed Jan. 28, 2014: pp. 1-31.

(Continued)

*Primary Examiner* — Daniel S Larkin
*Assistant Examiner* — Anthony W Megna Fuentes
(74) *Attorney, Agent, or Firm* — Jakub M. Michna (57) ABSTRACT

A wellbore tool for determining a speed of sound of a fluid sample, such as a hydrocarbon sample or a wellbore fluid, is described herein. The wellbore tool includes a photoacoustic system for analyzing the fluid sample. The photoacoustic system includes a laser system that generates a laser pulse, an interface disposed between the fluid sample and the laser system, and an acoustic detector that receives an acoustic pulse that is generated in response to absorption of the laser pulse. The acoustic pulse is generated when the laser pulse is absorbed by the fluid sample or the interface. This acoustic pulse then moves through the fluid sample and is detected by the acoustic detector. The acoustic pulse is then used to determine a speed of sound of the fluid sample.

17 Claims, 8 Drawing Sheets

(58) Field of Classification Search
USPC .................................. 73/152.28, 24.01–24.02
See application file for complete search history.

(56) References Cited

U.S. PATENT DOCUMENTS

| | | | |
|---|---|---|---|
| 6,672,163 B2 | 1/2004 | Han et al. | |
| 6,678,050 B2 | 1/2004 | Pope et al. | |
| 7,114,562 B2 | 10/2006 | Fisseler et al. | |
| 7,387,021 B2 | 6/2008 | DiFoggio | |
| 7,520,158 B2 | 4/2009 | DiFoggio | |
| 7,614,302 B2 | 11/2009 | DiFoggio et al. | |
| 7,644,993 B2 | 1/2010 | Kaminsky et al. | |
| 7,708,067 B2 | 5/2010 | Treviranus et al. | |
| 7,781,737 B2 | 8/2010 | Zhdaneev | |
| 7,821,635 B2 | 10/2010 | Pope et al. | |
| 7,828,058 B2 | 11/2010 | Fielder | |
| 7,835,003 B2 | 11/2010 | Jiang et al. | |
| 7,913,806 B2 | 3/2011 | Pabon et al. | |
| 8,037,747 B2 | 10/2011 | DiFoggio | |
| 8,586,913 B2 | 11/2013 | Zhou et al. | |
| 2005/0160791 A1* | 7/2005 | Kung | G01N 21/05 73/24.02 |
| 2005/0223808 A1 | 10/2005 | Myers et al. | |
| 2005/0276285 A1* | 12/2005 | Huang | H01S 3/115 372/10 |
| 2006/0266109 A1 | 11/2006 | DiFoggio | |
| 2008/0247425 A1* | 10/2008 | Welford | H01S 3/042 372/10 |
| 2009/0288474 A1* | 11/2009 | Kalkman | A61B 5/0095 73/24.02 |
| 2010/0011836 A1* | 1/2010 | Kalkman | G01N 21/1702 73/24.02 |
| 2010/0147051 A1* | 6/2010 | Tobias | G01N 21/1702 73/24.02 |
| 2010/0195679 A1* | 8/2010 | Kroupa | H01S 3/025 372/10 |
| 2011/0016962 A1 | 1/2011 | DiFoggio | |
| 2011/0023594 A1 | 2/2011 | Pelletier et al. | |
| 2011/0191027 A1 | 8/2011 | Pfutzner et al. | |
| 2012/0055232 A1* | 3/2012 | Thorson | G01N 21/1702 73/24.02 |
| 2012/0167693 A1 | 7/2012 | Asao | |
| 2012/0269214 A1* | 10/2012 | Li | H01S 3/0627 372/11 |
| 2013/0056626 A1 | 3/2013 | Shen et al. | |
| 2013/0145813 A1 | 6/2013 | Pleban | |
| 2015/0211983 A1 | 7/2015 | Speck et al. | |

FOREIGN PATENT DOCUMENTS

| | | |
|---|---|---|
| WO | 2012005725 | 1/2012 |
| WO | 2012030418 A1 | 3/2012 |
| WO | 2013090108 | 6/2013 |

OTHER PUBLICATIONS

Andrews et al., "Revealing Reservoir Secrets Through Asphaltene Science," Oilfield Review, Winter 2012/2013: pp. 14-25.
Chaudhuri et al., "An Algorithm for Determining Volume Fractions in Two-Phase Liquid Flows by Measuring Sound Speed," Journal of Fluids Engineering, vol. 134(10): pp. 101301-1-101301-7.
Fujisawa et al., "Development and Applications of Ruggedized VIS/NIR Spectrometer System for Oilfield Wellbores," Photonic Sensors, 2013, vol. 3(4): pp. 289-294.
"Insitu Fluid Analyzer," Schlumberger Brochure, 2008: pp. 1-8.
Kharrat et al., "Asphaltene Content Measurement Using an Optical Spectroscopy Technique," energy & fuels, 2013, vol. 27: pp. 2452-2457.
McCain et al., "Coefficients of Isothermal Compressibility of Reservoir Oils," Petroleum Reservoir Fluid Property, PennWell Corporation: Tulsa, 2011: pp. 54-73.
Michaelian et al., "Photoacoustic FT-i.r. spectra of separated western Canadian coal macerals: Analysis of the CH stretching region by curve-fitting and deconvolution," Fuel, Oct. 1990, vol. +–: pp. 1271-1275.
Mullins, "Asphaltenes and equilibrium fluid distributions," "Compartments" and "Oil chemistry," The Physics of Reservoir Fluids: Discovery Through Downhole Fluid Analysis, Schlumberger: Sugar Land, 2008: pp. 15-24 and pp. 43-46 and pp. 82-100.
Parker et al., "Photoacoustic effect in strongly absorbing fluids," Ultrasonics, Jan. 1991, vol. 29: pp. 63-67.
Ruiz-Morales et al., "Polycyclic Aromatic Hydrocarbons of Asphaltenes Analyzed by Molecular Orbital Calculations with Optical Spectroscopy," Energy & Fuels, 2007, vol. 21: pp. 256-265.
Zhao et al., "Multiparameter measurement of absorbing liquid by time-resolved photoacoustics," Applied Optics, Mar. 2012, vol. 51(8): pp. 1061-1066.
International Search Report and Written Opinion for related PCT Application No. PCT/US2014/069770 dated Mar. 31, 2015, 16 pp.

* cited by examiner

FLUIDIC SPEED OF SOUND MEASUREMENT USING PHOTOACOUSTICS

CROSS-REFERENCE TO RELATED APPLICATIONS

This application is related to U.S. patent application Ser. No. 14/166,593, filed on Jan. 28, 2014 and entitled "Fluid Analysis by Optical Spectroscopy with Photoacoustic Detection," which is incorporated herein by reference in its entirety.

BACKGROUND

The speed of sound in a fluid is a valuable piece of information that can be used to determine other properties of the fluid. In the oil and gas industry, the speed in sound of a fluid has been obtained using an acoustic module with an acoustic source and an acoustic receiver. An acoustic wave is generated by the acoustic source and travels to the acoustic receiver. The speed of sound is determined using a time of travel between the source and the receiver. The time of travel is then divided by the distance between the acoustic source and the receiver. In many cases, measuring the time of travel is complicated because the acoustic wave that is generated by the acoustic source is long as compared to the distance between the acoustic source and the receiver. For this reason, the calculated speed of sound may not be reliable.

SUMMARY

Illustrative embodiments of the present disclosure are directed to a wellbore tool for determining a speed of sound in a fluid sample, such as a hydrocarbon sample or a wellbore fluid. The wellbore tool includes a photoacoustic system for analyzing the fluid sample. The photoacoustic system includes a laser system that generates a laser pulse, an interface disposed between the fluid sample and the laser system, and an acoustic detector that receives an acoustic pulse that is generated in response to absorption of the laser pulse. The acoustic pulse is generated when the laser pulse is absorbed by the fluid sample or the interface. This acoustic pulse then moves through the fluid sample and is detected by the acoustic detector. The acoustic pulse is then used to determine a speed of sound in the fluid sample.

Various embodiments of the present disclosure are also directed to a method for determining a speed of sound in a fluid sample. The method includes positioning a photoacoustic system within a wellbore. The photoacoustic system includes a laser system and an acoustic detector. The laser system is used to apply a laser pulse to an interface disposed between the fluid sample and the laser system. The acoustic detector is used to detect an acoustic pulse generated by absorption of the laser pulse. The speed of sound in the fluid sample is determined using the detected acoustic pulse.

DETAILED DESCRIPTION

Illustrative embodiments of the present disclosure are directed to a wellbore tool for determining a speed of sound in a fluid sample, such as a hydrocarbon sample or a wellbore fluid. The wellbore tool includes a photoacoustic system for analyzing the fluid sample. The system includes a laser system that generates a laser pulse, an interface disposed between the fluid sample and the laser system, and an acoustic detector that receives an acoustic pulse that is generated in response to absorption of the laser pulse. The acoustic pulse is generated when the laser pulse is absorbed by the fluid sample or the interface. This acoustic pulse then moves through the fluid sample and is detected by the acoustic detector. An acoustic pulse generated in this manner is shorter and better defined. Thus, the acoustic pulse provides for simpler interpretation of the resulting electrical signal and a more accurate speed of sound measurement. Details of further embodiments are provided below.

Figure 1:
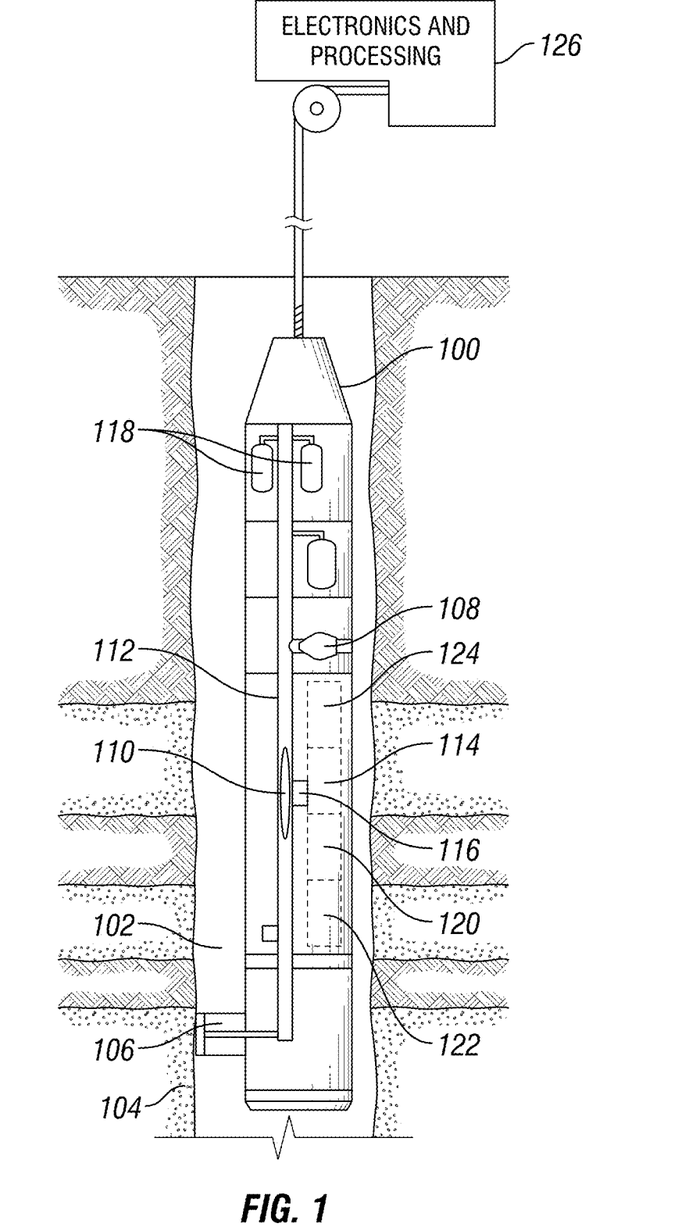
FIG. 1 shows a wellbore tool for fluid analysis in accordance with one or more embodiments.

Illustrative embodiments of the present disclosure are directed to oil field and gas field wellbore applications, such as wireline logging applications. FIG. 1 shows a wellbore tool 100 that incorporates a photoacoustic system. The wellbore tool 100 is a wireline tool and is suspended within a wellbore 102 that traverses an earth formation 104. The tool 100 may be suspended within the wellbore using a multiconductor cable that is spooled on a winch at the surface. In this embodiment, the wireline tool 100 draws a fluid sample (e.g., formation fluid or wellbore fluid) into the tool and analyzes the sample within the tool. In accordance with one or more embodiments, the wireline tool 100 includes a formation tester 106 having a selectively extendable probe assembly. The selectively extendable probe assembly is configured to fluidly couple to an adjacent formation 104 and to draw fluid samples from the formation. A pump 108 is used to pass a fluid sample 110 through the probe assembly and into a flow line 112 within the tool 100.

The wireline tool 100 also includes a photoacoustic system 114 for performing speed of sound measurements in the fluid sample 110 within the flow line 112. The photoacoustic system 114 includes at least one acoustic detector (e.g., a transducer), optics, and a pulsed laser system, such as a pulsed laser as described in, for example, International Patent Application Publication No. WO 2013/090108, published on Jun. 20, 2013, which is incorporated by reference herein in its entirety. The photoacoustic system and its components (e.g., the laser system and the transducer) can operate at the elevated temperatures typical of wellbore environments (e.g., temperatures greater than 100° C., 150° C. or 200° C.). The photoacoustic system 114 is in optical or acoustic communication with the fluid sample 110 within the flow line 112 via an interface 116. Accordingly, the fluid sample 110 within the flow line 112 may be analyzed by the photoacoustic system 114. Once the fluid sample 110 is analyzed, the sample can be expelled through a port (not shown) or the sample may be sent to one or more fluid collecting chambers 118.

The wireline tool 100 also includes several other systems that support the photoacoustic system 114. For example, the wireline tool 100 includes a power system 120 to provide power to the various components of the system (e.g., the laser and the acoustic detector). Also, the wireline tool 100 may include an amplification system 122 to amplify any electric signals that are output from the photoacoustic system 112. This electric signal may be representative of a detected acoustic pulse that is generated by laser light that is absorbed by the fluid sample or the interface. Furthermore, the wireline tool may include a telemetry system 124 to provide communication between the wireline tool and surface electronics and processing systems 126. In one example, the telemetry system 124 communicates the electrical signal from the photoacoustic system 114 to the surface.

Various embodiments of the present disclosure are not limited to the wireline tool 100 shown in FIG. 1. For example, one or more embodiments of the present disclosure may also be used in drilling applications, such as logging-while-drilling (LWD) systems or measurement-while-drilling (MWD) systems. In one particular embodiment, the LWD system includes a sampling-while-drilling system (e.g., the sampling-while-drilling system is part of an LWD tool suite). In the sampling-while-drilling system, a fluid sample may be drawn into the system from the formation and analyzed within the tool, in a similar manner to the wireline tool 100 of FIG. 1. Further details of sampling-while-drilling systems are provided in U.S. Pat. No. 7,114,562, issued on Oct. 3, 2006 and entitled "Apparatus and Method for Acquiring Information while Drilling." Furthermore, the tools described above can be used with any suitable means of conveyance, such as drill pipe, armored cable, or coiled tubing.

Figure 2:
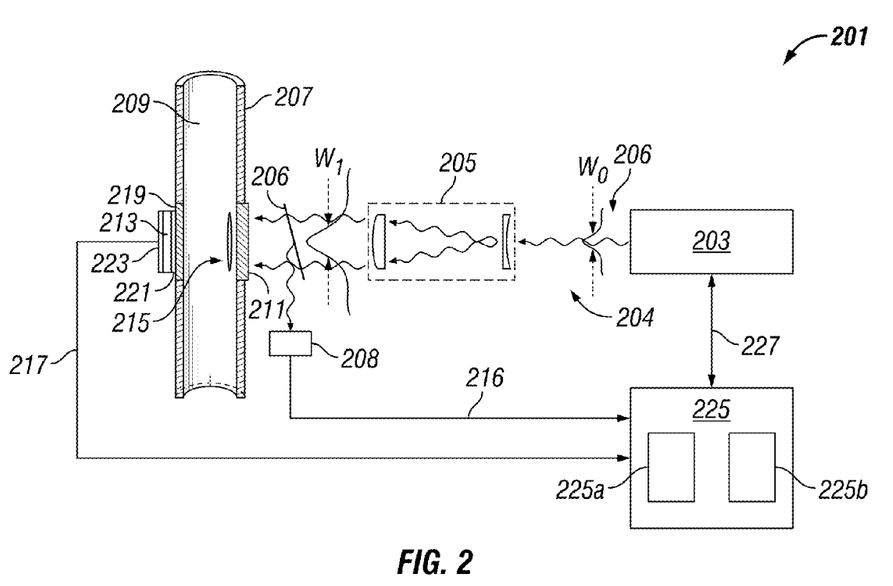
FIG. 2 shows a photoacoustic system in accordance with one or more embodiments.
Figure 7:
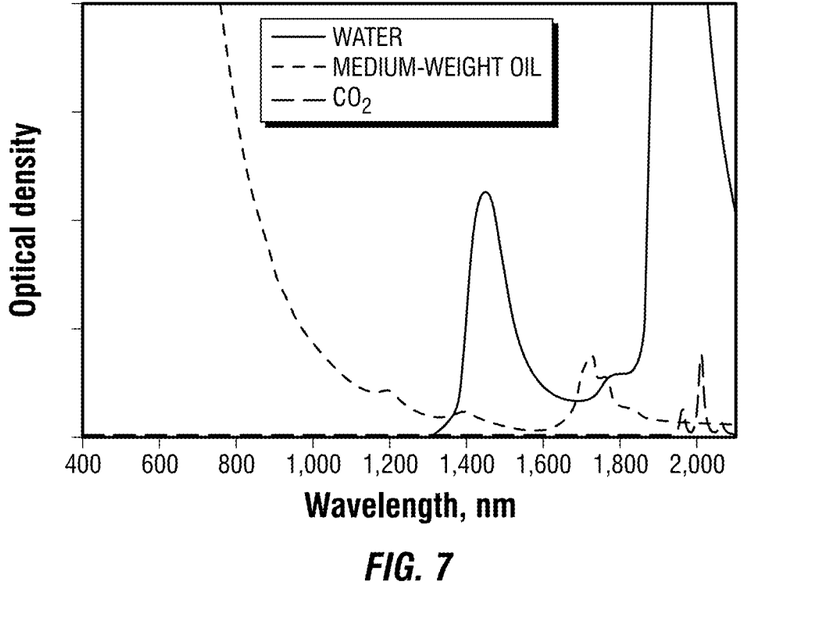
FIGS. 7-9 show absorption spectra for several different fluids in accordance with one or more embodiments.

FIG. 2 shows an illustrative example of a photoacoustic system 201 in accordance with one or more embodiments. FIG. 1 shows an example of a flow line based photoacoustic system 201 that employs a pulsed laser system 203 for conducting speed of sound measurements in a fluid of interest. In accordance with one or more embodiments, the photoacoustic system 201 includes a processing system 225, a pulsed laser system 203, a beam shaper 205, a beam sampler 206, a flow line 207 that serves as a fluid vessel for containing the fluid 209 under test. The flow line 207 further includes an interface 211 and an acoustic detector 213. In one embodiment, the interface 211 can be a material that is transparent to laser light (e.g., a window). In other embodiments, the interface 211 is an absorbing material that absorbs laser light and produces an acoustic pulse. As shown in FIG. 2, the interface 211 is disposed between the fluid 209 and the laser system 203. The pulsed laser system 203 emits one or more laser pulses 204 each having a wavelength $\lambda_{pulse}$ and a beam diameter w0. For example, in accordance with one or more embodiments, the wavelength $\lambda_{pulse}$ of the laser pulse is about 1390 nm, which leads to an absorption coefficient in water of 10 $cm^{-1}$. In some embodiments, the wavelength of the laser pulse is selected so that the pulse is absorbed by the fluid sample or by the interface. Examples of absorption spectra for different fluid constituents, such as water, medium-weight oil and carbon dioxide, are shown in FIG. 7. The laser beam diameter w may be defined as the $1/e^2$ diameter of the transverse spatial mode of the laser beam emitted from the laser system 203. For example, in the case of a transverse electromagnetic mode 0,0 ($TEM_{00}$), the output pulses of the laser system 203 may have an intensity distribution 206 that is Gaussian-shaped as measured along a direction that is perpendicular to the direction of pulse propagation (right-to-left direction in FIG. 2).

After generation by the laser system 203, the laser pulse 204 is directed to the beam shaper 205 that comprises a series of beam shaping optics that may be any collection of optics known in the art (e.g., lenses, mirrors, spatial filters, or the like). For example, the beam shaper 205 of FIG. 2 shows a lens pair that acts as a beam expanding telescope designed to expand the laser beam diameter from the laser output diameter $w_0$ to an expanded diameter $w_1$. In accordance with one or more embodiments, the optics used by the beam shaper 205 may be chosen to produce an expanded diameter w1 that is much larger than a characteristic length scale d. For fluids characterized by an absorption coefficient that is large relative to the light path length (defined as the maximum distance the light may travel through the fluid, e.g., the width of the flow line), the characteristic length scale d may be the penetration depth of the laser pulse into the fluid under test, where the penetration depth is defined as the depth within the fluid at which the intensity of the laser pulse is reduced to 1/e of its initial value. However, if the absorption coefficient is very small relative to the light path length within the flow line, the characteristic length scale d may alternatively be the light path length. After passing through the beam shaper 205, the laser pulse 204 is passed through the beam sampler 206. The beam sampler 206 redirects some of the light to an optical detector 208, such as a photodiode. The optical detector 208 is used to detect when the laser pulse is emitted by the laser system 203. An electric signal 216 representative of the laser pulse is provided from the optical detector 208 to the processing system 225. The remainder of the laser pulse 204 passes through the beam sampler 206 and is transmitted into the interface 211.

In embodiments where the interface 211 is a window, the laser pulse 204 passes through the window and is absorbed by the fluid 209. The material for window 211 may be chosen such that it is largely transparent at the laser wavelength $\lambda_{pulse}$ and further may also be largely transparent at any other wavelengths that may be used for the analysis (e.g., glass and sapphire). The laser pulse 204 is at least partially absorbed by the fluid thereby causing an excitation of the fluid's constituent molecules. The abrupt relaxation of the molecules in the fluid sample generates an acoustic pulse in a portion 215 of the fluid. The acoustic pulse propagates as an acoustic wave through the fluid 209 and is detected by the acoustic detector 213. In accordance with one or more embodiments, the acoustic detector 213 may be an ultrasonic transducer (e.g., that uses a piezoelectric element or the like). Furthermore, to minimize acoustic mismatches between the fluid and the detector, the acoustic detector 213 may be coupled to the fluid through a detector window 219 and/or through an acoustically matched layer 221, such as VITON™ rubber or polyether ether ketone (PEEK). Furthermore, in some embodiments, an absorbing backing material layer 223 that is acoustically matched to the detector window may be placed on the far side of the acoustic detector 213 to reduce ringing effects in the detector.

In other embodiments, the interface 211 is an absorbing material. The laser pulse 204 passes into the absorbing material and is at least partially absorbed by the material, thereby causing an excitation of the material's constituent molecules. The abrupt relaxation of the molecules in the absorbing material generates an acoustic pulse in a portion of the material. The acoustic pulse propagates through the absorbing material and into the fluid 209 as an acoustic wave. The acoustic wave propagates through the fluid 209 and is detected by the acoustic detector 213. In some embodiments, the absorbing medium is used to generate a thermal transient in the fluid 209. When the absorbing material absorbs the laser pulse, the material generates heat that is thermally transferred to the fluid 209. The heat transfer to the fluid produces thermal excitation and relaxation within the fluid 209 that, in turn, generates an acoustic pulse that travels through the fluid and to the acoustic detector 213. The absorbing material may include black anodized aluminum, graphite, carbon black or glass impregnated with laser absorbing dies, such as IR-1048. The thickness of the absorbing material may be chosen so that the absorption coefficient at the laser wavelength (given in $cm^{-1}$) times the thickness is much greater than 1. For example, for carbon black at 1064 nm, the absorption coefficient (alpha) is approximately 10000 $cm^{-1}$. Thus, a thickness greater than 1 micron will absorb at least approximately 37% of light entering the carbon black material. In illustrative embodiments, a thickness of several times 1 micron would be chosen to ensure that the light is fully absorbed.

The acoustic detector 213 detects the acoustic wave and generates an electrical signal 217 that corresponds to the detected acoustic wave. Electrical signals 216 and 217 may then be routed or transmitted to processing system 225 for further processing. The processing system 225 includes one or more memories 225a and one or more processors 225b. Accordingly, the processing system 225 may store the electrical signals 216 and 217 in the form of laser pulse data and acoustic pulse data and then further process the data (e.g., to determine a speed of sound in the fluid under test). An example of a detected signal is described below in more detail with reference to FIG. 4.

In some embodiments, the processing system 225 is configured to send/receive control signals to/from the laser system 203, respectively. For example, the processing system 225 may send control signals to the laser system to cause one or more pulses to be emitted from the laser system 203 in a precisely timed manner and may send control signals that control the particular wavelength of the laser pulse. Thus, in accordance with one or more embodiments, programming stored on the memory in the form of computer readable instructions, when executed by the processor, cause the laser system 203 to emit several pulses at several different wavelengths. The acoustic data generated by one or more laser pulses at one or more wavelengths may then be acquired and stored by the processing system. The acoustic data can be used to determine the speed of sound in the fluid. Furthermore, the acoustic data generated at each wavelength can be used to determine other properties of the fluid, such as an absorption spectrum of the fluid, as described in, for example, U.S. patent application Ser. No. 14/166,593, filed on Jan. 28, 2014 and entitled "Fluid Analysis by Optical Spectroscopy with Photoacoustic Detection." Accordingly, the same photoacoustic system can be used to determine both the speed of sound and to perform photoacoustic spectroscopy, which can determine the various components and concentrations of components within the fluid sample.

As described above, the photoacoustic system 201 may be incorporated into a downhole fluid sampling tool and the flow line 207 may be configured to couple with the flow line of the tool. Thus, the photoacoustic system 301 may be used to characterize formation fluids or any other downhole fluid of interest (e.g., wellbore, fluids, wellbore muds, and formation fluids) that may be sampled by the tool. Such a configuration was described above in FIG. 1.

Figure 3:
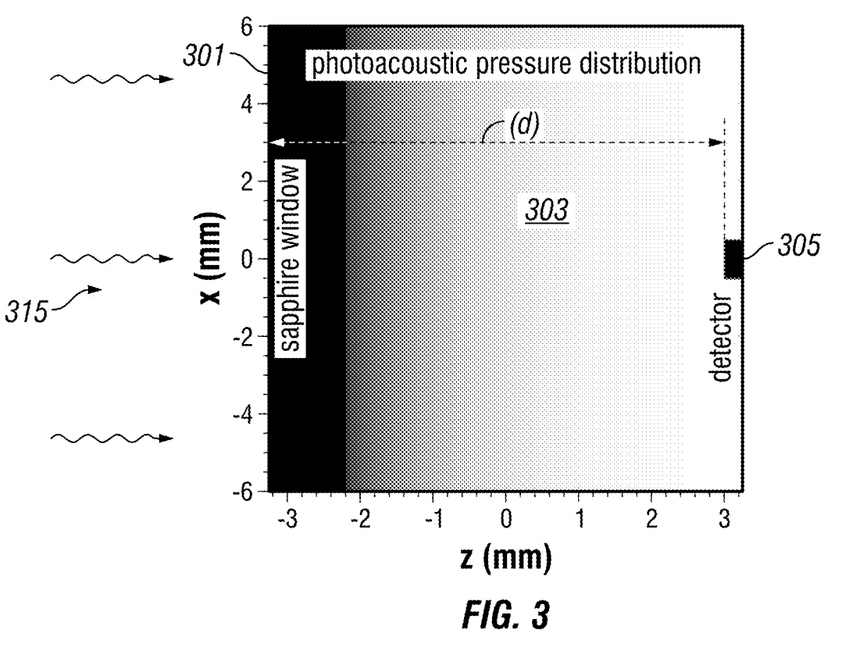
FIG. 3 shows a photoacoustic pressure distribution in accordance with one or more embodiments.
Figure 4:
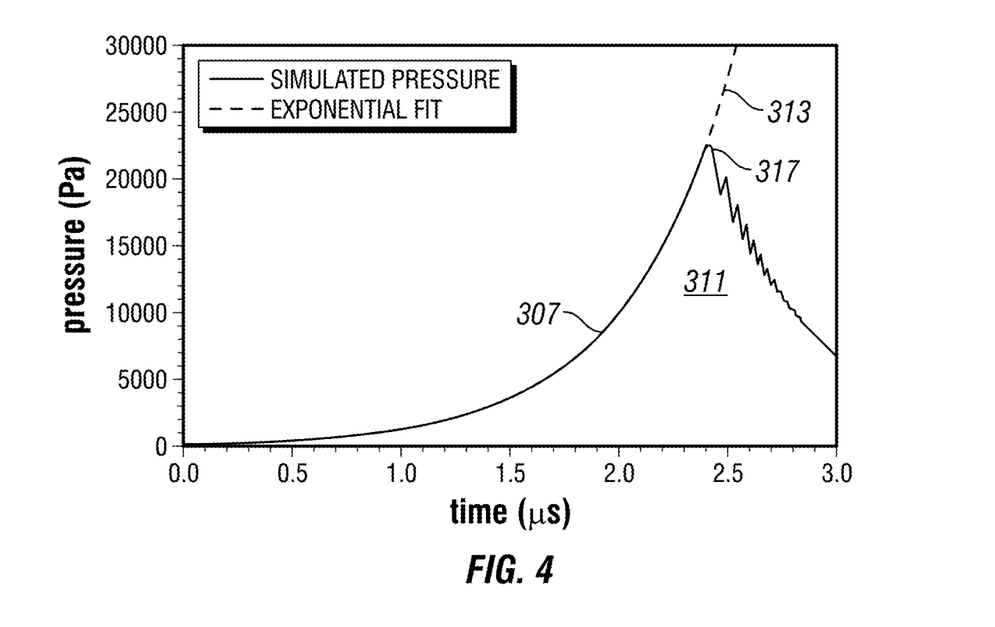
FIG. 4 shows a pressure data in accordance with one or more embodiments.

FIGS. 3 and 4 show a photoacoustic system and simulated test data numerically simulated using the system, respectively. In particular, the data shown in FIG. 4 represents time resolved acoustic data that may be detected using the photoacoustic system shown in FIG. 3 (e.g., corresponding to the flow line arrangement shown in FIGS. 1 and 2). The photoacoustic system shown in FIG. 3 includes a sapphire window 301 that is approximately 1 mm in thickness located at a z position of approximately 2.8 mm. An acoustic detector 305 is mounted approximately 6 mm from the sapphire window (d). A volume 303 between the window 301 and the detector 305 is filled with water. In some embodiments, the volume is the volume within a flow line. In this simulation, a laser pulse 315 having a wavelength of 1390 nm is incident on the window from the left. As described above, the optical absorption of the laser pulse by the fluid leads to an excitation of the fluid that manifests as a propagating pressure disturbance in the fluid (also referred to herein as a photoacoustic pressure distribution, or as a pressure wave). In FIG. 3, the photoacoustic pressure distribution is shown as an intensity gradient in grayscale with a darker color indicating a higher pressure. After the photoacoustic pressure distribution is produced, it travels as a pressure wave 311 toward the acoustic detector 305. FIG. 4 shows a portion (e.g., waveform) of a time resolved acoustic signal that is detected as the pressure wave 311 traverses the detector. As can be seen from FIG. 4, in this example, the detector first detects an exponentially rising pressure 307 followed by an abrupt decrease in pressure as the photoacoustic pressure wave 311 passes the detector.

The speed of sound in the fluid under test can be determined using (i) a time of travel of the acoustic pulse within the fluid under test (e.g., between the interface and the detector) and (ii) the distance the acoustic pulse travels within the fluid (e.g., the distance between the interface and the detector). In particular, the speed of sound can be determined according to the following relationship:

$$c = \frac{d}{t} \quad (1)$$

where c is the speed of sound in the fluid, t is the time of travel, and d is the distance travelled. In the system of FIG. 3, the distance between the detector 305 and the interface (e.g., window) 301 is called out by letter d. This distance (d) is a known value. The time of travel (t) can be determined by measuring or determining the time elapsed between emission of the laser pulse and arrival of the acoustic pulse at the detector.

In various embodiments, the processing system determines the speed of sound in the fluid under test by receiving (i) the electrical signal from the acoustic detector representative of the acoustic pulse (e.g., electrical signal 217 in FIG. 2) and the electrical signal from the optical detector representative of the laser pulse (e.g., electrical signal 216 in FIG. 2). To this end, in various embodiments, the processing system identifies a time that corresponds to a peak amplitude within electric signal from the acoustic detector (e.g., peak amplitude 317 of waveform in FIG. 3). The peak of the waveform corresponds to absorption occurring at the interface between the window and the flow line and can be the time used to calculate the speed of sound. Similarly, the processing system identifies a time corresponding to a peak amplitude of the electric signal from the optical detector that represents the emission of the laser pulse. The processing system then determines a time difference between the two times to determine the time of travel (t). In various embodiments, this time of travel is compensated by subtracting the time of travel of the acoustic pulse through one or more interfaces (e.g., windows or absorbing materials). The time of travel through an interface can be determined using the thickness of the interface and the speed of sound within the interfaces. The thickness and speed of sound of the interface are typically known values.

Various other properties of the fluid can be determined from the speed of sound of the fluid, such as compressibility of the fluid. The compressibility of a fluid ($\beta$), is related to the speed of sound (c) by:

$$c = \sqrt{\frac{1}{\rho\beta}} \quad (2)$$

where $\rho$ is the density. Thus, according to Equation 2, the compressibility ($\beta$) of the fluid can be determined from a measurement of the speed of sound and the fluid density.

In some embodiments, the density is obtained from a separate independent density measurement. For example, the density can be obtained from a beta particle measurement, such as the measurement described in U.S. Pat. No. 8,586,913, issued on Nov. 19, 2013 and entitled "Fluidic Density Measurements Based on Beta Particles Detection," which is hereby incorporated by reference in its entirety. In other embodiments, rather than using an independent measurement of the density, the density can be determined by using photoacoustic spectroscopy as described in, for example, U.S. patent application Ser. No. 14/166,593, filed on Jan. 28, 2014 and entitled "Fluid Analysis by Optical Spectroscopy with Photoacoustic Detection." In this manner, the same photoacoustic system can be used to determine both the speed of sound and the density of the fluid under test. Photoacoustic spectroscopy can be used to determine the various components and concentrations of components within the fluid sample, which, in turn, can be used to determine gas-oil ratio (GOR) and density for the fluid sample. Compressibility is also correlated with GOR and can be used as an independent estimation of GOR.

Knowledge of the compressibility of an oil ($\beta$) is useful for several applications within the oilfield. For example, compressibility can be used to estimate fluid properties above the bubble point of the fluid. If the density of oil at the bubblepoint ($\rho_b$) and the bubblepoint pressure ($p_0$) are known, the density of oil at other pressures (p) above the bubblepoint is given by:

$$\rho = \rho_b e^{\beta(p-p_0)} \quad (3)$$

Compressibility can also be used for analysis of pressure transients. In particular, the continuity equation for radial flow is as follows:

$$\frac{\partial^2 p}{\partial r^2} + \frac{1}{r}\frac{\partial p}{\partial r} = \frac{\phi\mu\beta}{k_r}\frac{\partial p}{\partial t} \quad (4)$$

where $k_r$ is the radial permeability, $\phi$ is the porosity, and $\mu$ is the viscosity.

Additionally, compressibility can be used in material balance equations in evaluating reservoir performance. Also, compressibility can be used to determine the undersaturated oil formation volume factor of a formation fluid above its bubble point. Furthermore, compressibility can also be used to determine American Petroleum Institute oil gravity, gas specific gravity, solution gas oil temperature, bubble point pressure, reservoir temperature and reservoir pressure. One or more of these parameters can be inverted to determine other parameters. Details of such correlations can be found in, for example, W. McCain et al., Petroleum Reservoir Fluid Property Correlations, PennWell Corporation (2011).

The speed of sound can also be used to determine other fluid properties. For example, a speed of sound measurement and temperature measurement of a two phase fluid can be used to predict volume fractions of the two phases (assuming the compressibility and density of the individual phases are known or can be estimated). Details of this determination can be found in, for example, Chaudhari et al., "An Algorithm for Determining Volume Fractions in Two-Phase Liquid Flows by Measuring Sound Speed," J. Fluids Eng. 134(10), 101301 (2012).

Figure 5A:
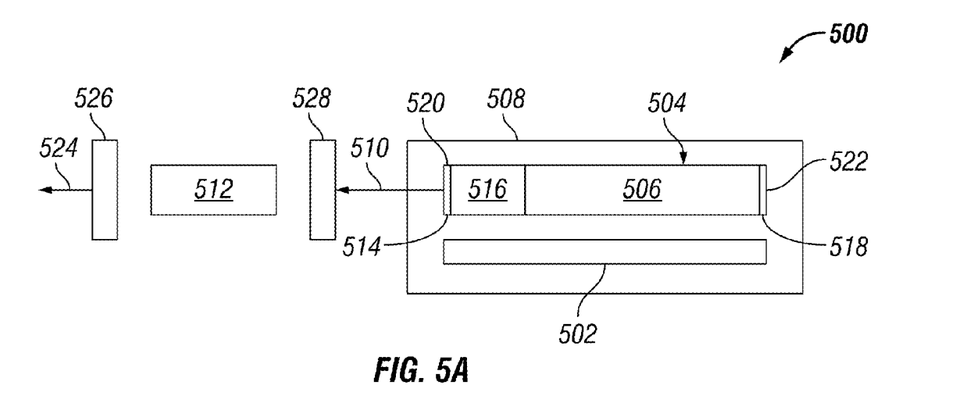
FIGS. 5A-5E show pulsed laser sources for a wellbore tool in accordance with one or more embodiments.
Figure 5B:
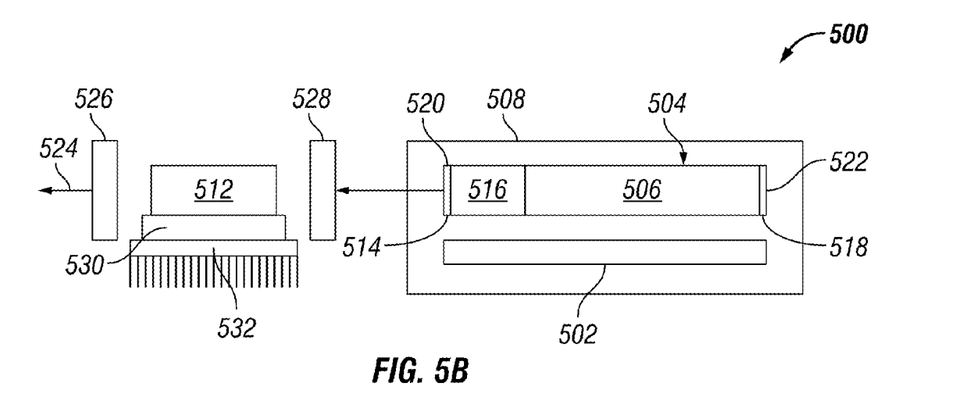
Figure 5C:
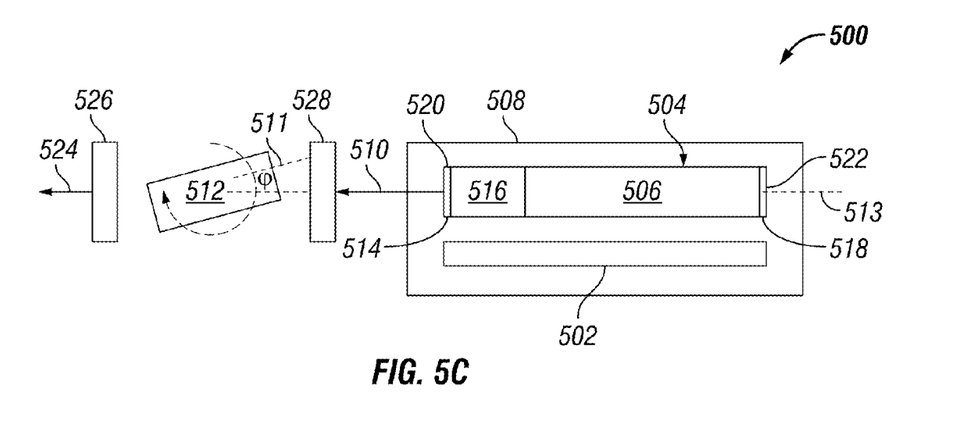

FIGS. 5A-5C show diagrams of pulsed laser sources 500 in accordance with one or more embodiments. These sources may be deployed as a pulsed laser source 303 (e.g., as described above in reference to FIGS. 2-3 and may also be deployed within wellbore tools, such as the one described above with reference to FIG. 1. As described in more detail below, the laser sources 500 use a monolithic Q-switched architecture that is adapted for stable wellbore use. In accordance with one or more embodiments, when the laser source 500 is exposed to temperatures between about room temperature and about 200° C., the laser source 500 outputs laser pulses having pulse energies (e.g., 8 mJ, 14 mJ, 22 mJ, etc.) substantially independent of the temperature. For example, from about room temperature to about 200° C., the laser source 500 outputs laser pulses having pulse energies with a standard deviation within about 10 percent. Also, in accordance with one or more embodiments, the laser source 500 may output laser pulses even when subjected to shocks (e.g., a 500 g shock) and/or vibrations (e.g., a 0.5 $g^2/\sqrt{Hz}$ vibration).

The laser sources 500 of FIGS. 5A-5E include a pump source 502 such as, for example, a flash lamp, an arc lamp, an LED, a laser diode, and/or any other suitable pump source. The example pump source 502 may be adjacent a monolithic body 504 to transversely pump a solid state gain medium 506 of the monolithic body 504. In the illustrated examples, a reflective cavity 508 substantially encloses the monolithic body 504 and the pump source 502. In some examples, the reflective cavity 508 is defined by a substantially transparent (e.g., glass) cylinder at least partially covered by a diffuse reflector such as barium sulfate, Teflon, and/or any other suitable diffuse reflector. In other examples, the reflective cavity 508 may be an elliptical mirror.

The example monolithic body 504 of FIGS. 5A-5E includes a first reflector 514, a Q-switch 516, a solid state gain medium 506 and a second reflector 518. In the illustrated example, a first end of the Q-switch 516 is coupled to the solid state gain medium 506. In the illustrated example, the first reflector 514 is disposed on a first end 520 of the monolithic body 504 and the second reflector 518 is disposed on a second end 522 of the monolithic body 504. The first reflector 514 is coupled to the Q-switch 516, and the second reflector 518 is coupled to the solid state gain medium 506. In some examples, the first reflector 514 and/or the second reflector 518 are film coatings.

In the illustrated example, the first reflector 514 and the second reflector 518 provide an optical resonator (e.g., they reflect light in a closed path). In some examples, reflective surfaces of the first reflector 514 and the second reflector 518 are substantially parallel to each other. In other examples, the first reflector 514 and the second reflector 518 are curved. In some such examples, the first reflector 514 and the second reflector 518 are curved such that the first reflector 514 and the second reflector 518 are substantially confocal or substantially concentric.

In some examples, the solid state gain medium 506 is a material in a solid state such as, for example, a chromium doped beryllium aluminum oxide crystal ($Cr^{3+}:BeAl_2O_4$) ("alexandrite"), a neodymium-doped yttrium aluminum garnet crystal ($Nd:Y_3Al_5O_{12}$) ("Nd:YAG") or any other suitable material. In some examples, the solid state gain medium 606 includes a dopant element such as Nd, Yb, Er, Ti, Tm, and/or any other suitable dopant element.

During operation of the laser 500, the pump source 502 causes a population inversion in the solid state gain medium 506 which in turn causes the solid state gain medium 506 to emit laser light having a wavelength the depends on the material of the solid state gain medium 506. For example, if the solid state gain medium 506 is Nd:YAG, the solid state gain medium 506 produces light having a wavelength of 1064 nm.

In the illustrated example, the second reflector 518 is about 100 percent (e.g., 95%, 98%, 99%, 99.9%, etc.) reflective to the light emitted by the solid state gain medium 506 (e.g., 1064 nm for Nd:YAG). The example first reflector 514 has a reflectivity of less than 100 percent (e.g., 80%, 90%, etc.) to the light emitted by the solid state gain medium 506.

In accordance with one or more embodiments, such as the example illustrated in FIGS. 5A-5C, the Q-switch 516 is a passive Q-switch such as, for example, a saturable absorber. A coefficient of thermal expansion of the Q-switch 516 may be substantially equal to a coefficient of thermal expansion of the solid state gain medium 506. In some examples, the Q-switch 516 is implemented using a Cr:YAG crystal. One end of the Q-switch 516 may be non-adhesively bonded (e.g., diffusion bonded, optical contact bonded, etc.) to an end of the solid state gain medium 506. In some such examples, the first reflector 514 is disposed on an opposing end of the Q-switch 516. Some embodiments of the laser do not include the Q-switch 516. As described in greater detail below, the Q-switch 516 prevents the laser from outputting a laser pulse until a population inversion in the solid state gain medium 506 reaches a predetermined level (e.g., a peak level).

During operation, the Q-switch 516 prevents the laser 500 from outputting or transmitting the laser pulse until the population inversion in the solid state gain medium 506 reaches a predetermined level (e.g., a peak level). For example, the Q-switch 516, a saturable absorber, is substantially non-transparent until the population inversion reaches the predetermined level. Once the population inversion reaches the predetermined level, the Q-switch 516 becomes at least partially transparent and the laser pulse passes through the Q-switch 516 and the first reflector 514.

FIG. 5A shows a pulsed laser source 500 that includes an optical parametric oscillator (OPO) that itself includes an external nonlinear crystal 512 that is disposed between reflector 528 and reflector 526. In the illustrated example, the reflector 526, the nonlinear crystal 512, and the reflector 528 may be disposed outside of the reflective cavity formed by the monolithic body 504. Furthermore, the OPO is positioned along a path of the first laser pulse 510 so that the first laser pulse 510 serves as a pump laser pulse that optically pumps the OPO to generate a second set of laser pulses at one or more modified wavelengths, where the modified wavelengths depend on the wavelength of the first laser pulse and one or more properties of the nonlinear crystal 512 of the OPO. As described in more detail below, the one or more properties of the nonlinear crystal may be controlled by a processing system to allow for wide tunability of the modified wavelength.

In the illustrated example, the reflectors 526 and 528 reflect a fundamental wavelength of the first laser pulse 510. As a result, the first laser pulse 510 passes through the reflector 528, and the nonlinear crystal 512 of the OPO converts the first laser pulse 510 to light having a wavelength different than the first laser pulse 510. In the illustrated example, the reflectors 526 and 528 provide an optical resonator for the light produced via the nonlinear crystal 512, and the laser 500 outputs a second laser pulse 524 via the reflector 526 of the OPO.

FIG. 5B illustrates a pulsed laser source 500 that includes an OPO that itself includes nonlinear crystal 512 that is coupled to a heat pump 530 (e.g., a Peltier thermoelectric device) and a heat sink 532 that controls temperature of the nonlinear crystal 512 of the OPO to achieve tunability of a phase matching condition. For example, phase matching may occur for second harmonic generation of light having a wavelength of 1064 nm by adjusting a temperature of a lithium triborate (LBO) crystal to 148° C.

FIG. 5C illustrates a pulsed laser source 500 that includes an OPO that itself includes a nonlinear crystal 512 that has a longitudinal axis 511 that is nonparallel to an optical axis 513 of the monolithic body 504. In the illustrated example, the nonlinear crystal 512 of the OPO is oriented such that the phase matching condition may be tuned by rotating the nonlinear crystal 512.

Figure 5D:
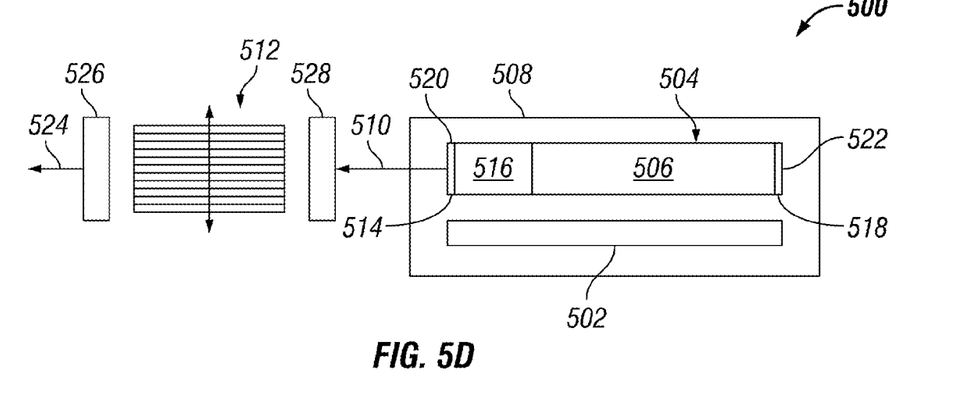

FIG. 5D illustrates a pulsed laser source 500 that includes an OPO that itself includes a nonlinear crystal 512 that is formed having several channels, each channel having a different poling period within the nonlinear crystal 512. Accordingly, when the first laser pulse 510 passes through a particular channel of the nonlinear crystal 512, the crystal will output a laser pulse having a wavelength that depends on the wavelength of the first laser pulse and the poling period of that particular channel. Thus, to alter the output wavelength, the nonlinear crystal 512 may be mechanically translated so that a different channel of the nonlinear crystal 512 having a different poling period is selected for pumping by the first laser pulse 510.

Figure 5E:
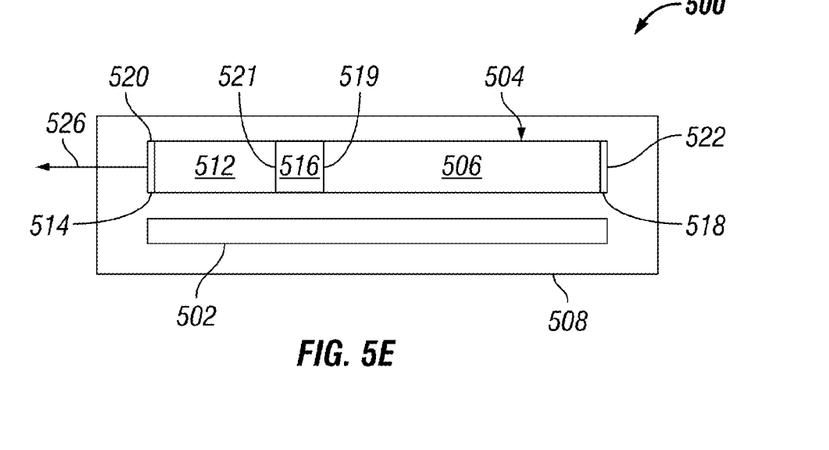

FIG. 5E illustrates a pulsed laser source 500 similar to that described above but further including a nonlinear crystal 512 that is integrated into the monolithic body 504. Accordingly, in this illustrated example, the monolithic body 504 includes a first reflector 514, a nonlinear crystal 512, a Q-switch 516, a solid state gain medium 506, and a second reflector 518. In the illustrated example, a first end 521 of the Q-switch 516 is coupled to the nonlinear crystal 512, and a second end 519 of the Q-switch 516 is coupled to the solid state gain medium 506. In the illustrated example, the first reflector 514 is disposed on a first end 520 of the monolithic body 504 and the second reflector 518 is disposed on a second end 522 of the monolithic body 504. The first reflector 514 is coupled to the nonlinear crystal 512, and the second reflector 518 is coupled to the solid state gain medium 506. In some examples, the first reflector 514 and/or the second reflector 518 are film coatings. In the illustrated example, the first reflector 514 and the second reflector 518 provide an optical resonator, as described above (e.g., in reference to FIGS. 5A-5D).

In this illustrated example, the nonlinear crystal 512 may be composed of Lithium triborate (LBO), potassium titanyl phosphate (KTP), beta-barium borate (BBO), lithium niobate (LN) and/or any other suitable material. In some examples, the nonlinear crystal 512 is a periodically poled material such as, for example, periodically poled lithium niobate (PPLN).

During operation of the laser 500, the pump source 502 causes a population inversion in the solid state gain medium 506 which in turn causes the solid state gain medium 506 to emit laser light having a wavelength the depends on the material of the solid state gain medium 506. The nonlinear crystal 512 converts the light produced via the solid state gain medium 506 to light having a modified wavelength that is different from the wavelength of the light produced via the solid state gain medium 506. For example, if the solid state gain medium 506 is Nd:YAG, the solid state gain medium 506 produces light having a wavelength of 1064 nm, which the nonlinear crystal 512 converts to light having a wavelength of, for example, 532 nm, 354 nm, or 266 nm.

In the illustrated example, one of the first reflector 514 or the second reflector 518 may be anisotropic. The first reflector 514 and the second reflector 518 are about 100 percent (e.g., 95%, 98%, 99%, 99.9%, etc.) reflective to the light emitted by the solid state gain medium 506 (e.g., 1064 nm for Nd:YAG). However, the example second reflector 518 has a reflectivity of about 100 percent (e.g., 95%, 98%, 99%, 99.9%, etc.) to the light produced via the nonlinear crystal 512 while the first reflector 514 has a reflectivity of less than 100 percent (e.g., 80%, 90%, etc.) to the light produced via the nonlinear crystal 512. Thus, the light produced via the solid state gain medium 606 is substantially reflected between the first reflector 614 and the second reflector 618 (i.e., the light is substantially contained in the optical resonator) while the light produced by the nonlinear crystal 512 (i.e., wavelength shifted light) is outputted via the first reflector 514. As a result, the laser 500 outputs a laser pulse 526 having a wavelength of the light produced by the nonlinear crystal 512.

In some examples, the laser source may be a laser source like that shown in FIG. 5E (i.e., one that employs a nonlinear crystal that is integrated into the monolithic body). In other examples, the laser source may employ an external OPO having its own nonlinear crystal and a monolithic body that does not employ a nonlinear crystal (e.g., like the examples illustrated in FIGS. 5A-5D). In yet other examples, the laser source may employ a monolithic body that includes a nonlinear crystal and may also employ an external OPO.

In some examples, the wavelength of the output laser pulse may be tuned by changing a phase matching, or quasi-phase matching, condition of the nonlinear crystal used within OPO. The phase matching condition is highly wavelength dependent and thus, for a given input pulse, the OPO will only efficiently generate output laser pulses at an output wavelength that satisfies the phase matching condition. Thus, a modification of the phase matching condition provides for a modification of the output pulse wavelength for any given input pulse wavelength. For example, as shown in FIG. 5C, the phase matching condition may be changed by altering the angle ϕ between the nonlinear crystal and the direction of the beam 510 entering the OPO.

In addition, the phase matching condition may be modified by altering what is known as the poling period of the nonlinear crystal (in cases where a periodically poled nonlinear crystal is employed). For example, in the illustrative embodiment shown in FIG. 5D, the crystal 512 has several channels, each channel with a different poling period, as described above. A desired phase matching condition may be selected by translating the crystal relative to the output (pump) beam 510.

In another example, the temperature of the nonlinear crystal may be changed in order to change the phase matching condition so as to tune the wavelength of the laser pulses output from the OPO. An example of this type of OPO system is shown in FIG. 5B. In this illustrative embodiment, a temperature control system (not shown) may be used to control a heat pump 530 (e.g., a Peltier thermoelectric device) that is attached to the nonlinear crystal 512. Likewise, in the monolithic design shown in FIG. 5E, a suitable temperature control system (not shown) may be employed to vary the temperature of the nonlinear crystal 512 and thus, to tune the output wavelength.

Figure 6:
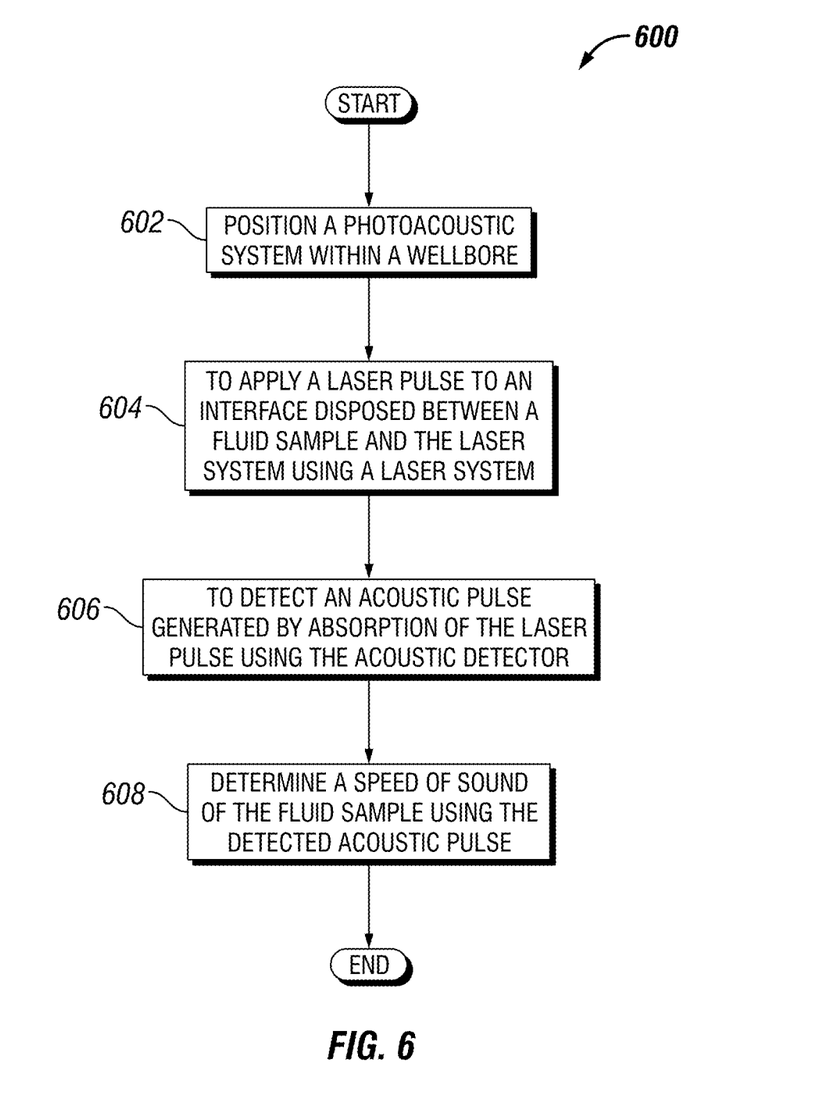
FIG. 6 shows a method for downhole fluid analysis in accordance with one or more embodiments.

FIG. 6 shows a method 600 for analyzing a fluid sample in accordance with one or more embodiments. In process 602, a photoacoustic system is positioned within a wellbore. The photoacoustic system includes a laser system and an acoustic detector. In accordance with one or more embodiments, the photoacoustic system may be a photoacoustic system as described above in, for example, FIG. 2. Furthermore, the photoacoustic system may be part of a larger wellbore tool, such as the one shown in FIG. 1). In some embodiments, before process 602 begins, the wellbore tool uses a selectively extendable probe assembly to draw formation fluid into the wellbore tool from a formation and into a flow line of the tool where it is analyzed.

In process 604, a laser pulse is applied to the fluid sample using the laser system of the photoacoustic system. The laser pulse may be generated from within a laser cavity of the laser. For example, the photoacoustic system may include a laser cavity formed from a single monolithic body that includes a first reflector, a Q-switch, a solid state gain medium, and a second reflector. An example of such a laser cavity formed from a monolithic body is described above in reference to FIGS. 5A-5C. The Q-switch may be used to modulate the quality factor of the solid state gain medium and thereby generate the laser pulse directly from the gain medium without a need for external chopper wheels or the like. Furthermore, the Q-switched solid state source allows for laser pulses having short durations (e.g., having durations in the range of 1-100 ns). In accordance with one or more embodiments, the Q-switch may be a passive Q-switch in the form of a saturable absorber that may be non-adhesively bonded to the end of the solid state gain medium (e.g., by way of diffusion bonding, optical contact bonding, etc.). In some examples, the generated laser pulses are directed by an optical system to a window in the photoacoustic system and enter the fluid under test. In accordance with one or more embodiments, the laser pulses are absorbed by the fluid thereby inducing an acoustic pulse in the fluid as described in further detail above in reference to FIGS. 3-4.

In process 606, the acoustic pulse is detected by an acoustic detector (e.g., a piezoelectric transducer or the like). In accordance with one or more embodiments, the acoustic detector detects the fluid pressure as a function of time thereby generating what is referred to herein as time-resolved acoustic pulse data. An example of time resolved acoustic pulse data is shown in FIG. 4 and is described above in the accompanying description.

In process 608, the detected acoustic pulse is used to determine a speed of sound in the fluid sample. For example, in various embodiments, the time of travel of the acoustic pulse is determined based on when the acoustic pulse arrives at the acoustic detector. This time of travel is then divided by a known distance travelled by the acoustic pulse to determine the speed of sound in the fluid.

Figure 8:
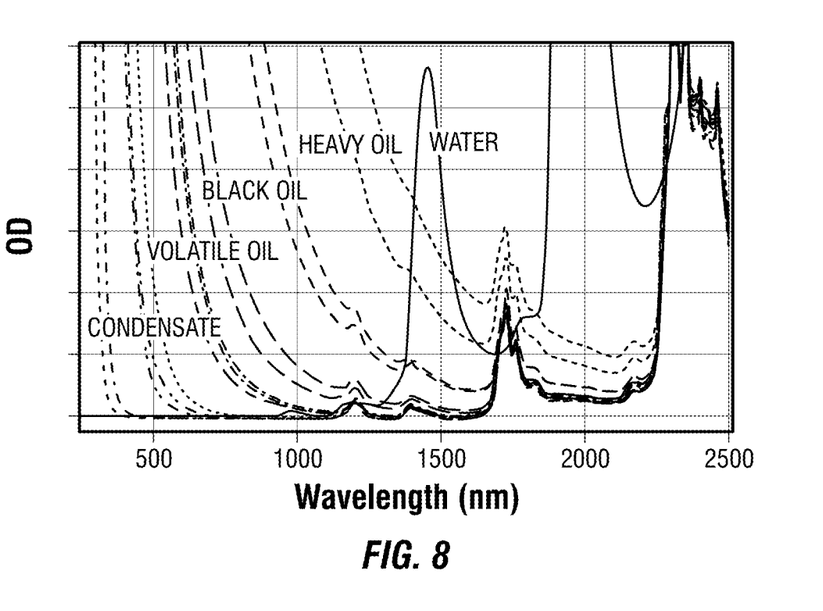
Figure 9:
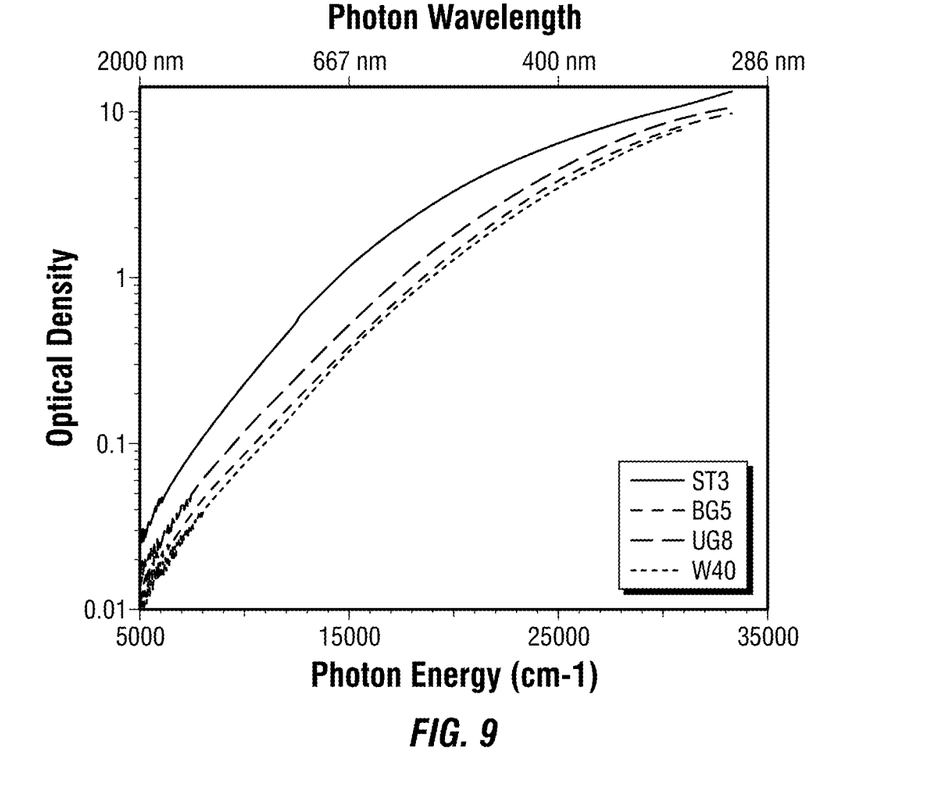

In the illustrative examples described above, the use of an OPO allows for the wavelength of the laser pulse to be tuned over a wide range of wavelengths. For a periodically poled lithium niobate crystal the wavelength may be tuned over a range of 1410 nm to 4335 nm. In another example, a doubled Nd:YAG system may allow for tuning over a range of 355 nm to 4500 nm. Other OPO crystals, such as chalcogenide (e.g., gallium selenide (Gase)), would allow for tuning at far infrared wavelengths (e.g., wavelengths at 1 to 20 microns and greater). Accordingly, the tunable, pulsed laser system coupled with a photoacoustic detection system allows for the determination of speed of sound in fluids over a wide range of wavelengths and thus allows for the system to perform measurements in any number of different fluids. For example, FIG. 7 shows examples of absorption spectra of several different types of fluids that may be characterized using the system. FIG. 7 shows absorption spectra for water, medium-weight oil, and CO2, while FIG. 8 shows absorption spectra for condensate, volatile oil, black oil, heavy oil and water. FIG. 9 shows absorption spectra for a number of different asphaltenes, as described in, for example, Ruiz-Morales et al., "Polycyclic Aromatic Hydrocarbons of Asphaltenes Analyzed by Molecular Orbital Calculations with Optical Spectroscopy," Energy and Fuels, 21, 256-265 (2007). As used herein, the term heavy oil refers to oils having an asphaltene content greater than about 5% by weight (5 wt. %.). As used herein, the term black oil refers to an oil having an asphaltene content of less than about 5 wt. % and also having more asphaltenes than a volatile oil or condensate. Furthermore, as referred to herein, the term asphaltene is defined to be the component of oil that is soluble in toluene but not soluble in an aliphatic solvent such as pentane.

The systems and methods disclosed herein generally relate to methods and systems for determining the speed of sound of unknown fluid samples (e.g., unknown unconventional hydrocarbon fluid samples). It will be appreciated that the same systems and methods may be used for performing subsurface analysis in fields such as oilfield, mining, water retrieval, or in any field where fluid sample characterization is desired. Furthermore, in accordance with one or more embodiments, the system may be deployed as a stand-alone analytical instrument (e.g., as a lab-based analytical instrument or as ruggedized unit for field work), or as part of a wellbore tool for in situ formation characterization (e.g., as part of a wireline tool, a logging while drilling ("LWD") tool, or a measurement while drilling ("MWD") tool). The systems and methods disclosed herein are not limited to the above-mentioned applications and these applications are included herein merely as a subset of examples.

Some of the processes described herein, such as (1) determining a speed of sound in a fluid sample using a detected acoustic pulse, (2) determining compressibility of the fluid sample using the speed of sound, (3) receiving an electric signal from an acoustic detector representative of an acoustic pulse, (4) receiving an electric signal from an optical detector representative of a laser pulse, (5) identifying a time corresponding to a peak amplitude of the electric signal from the acoustic detector, (6) identifying a time corresponding to a peak amplitude of the electric signal from the optical detector, (7) determining a time difference between the two times, and (8) controlling operation and tuning of the laser system, can be performed by a processing system.

In one embodiment, the processing system is located at the well site as part of surface equipment (e.g., the electronics and processing 126 in FIG. 1). The processing system communicates with the wellbore tool via, for example, an armored cable or mud pulse telemetry. In a second embodiment, the processing system is incorporated into the wellbore tool. In another embodiment, the surface equipment and wellbore tool each include processing systems. In yet another embodiment, however, the processing system is located remote from the well site at an office building or a laboratory to support the lab-based analytical instrument described above.

The term "processing system" should not be construed to limit the embodiments disclosed herein to any particular device type or system. In one embodiment, the processing system includes a computer system. The computer system may be a laptop computer, a desktop computer, or a mainframe computer. The computer system may include a graphical user interface (GUI) so that a user can interact with the computer system. The computer system may also include a computer processor (e.g., a microprocessor, microcontroller, digital signal processor, or general purpose computer) for executing any of the methods and processes described above (e.g., processes 1-8 listed above).

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. This memory may be used to store, for example, data from the wellbore tool.

Some of the methods and processes described above, including processes 1-8, as listed above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Additionally or alternatively, the processing system may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:
1. A wellbore tool comprising:
a photoacoustic system comprising:
  a laser system that is configured to generate a laser pulse;
  an interface disposed between a fluid sample and the laser system, wherein the interface is comprised of an absorbing medium that is configured to absorb the laser pulse such that an acoustic pulse is generated by the absorbing medium in response to the absorption an acoustic detector configured to receive the acoustic pulse that is generated in response to the absorption of the laser pulse; and a processing system configured to (i) receive an electric signal from the acoustic detector representative of the acoustic pulse and (ii) determine a speed of sound in the fluid sample using the electric signal.

2. The wellbore tool of claim 1, wherein the interface is a window that transmits the laser pulse to the fluid sample.

3. The wellbore tool of claim 1, wherein the processing system is configured to determine compressibility of the fluid sample using the speed of sound.

4. The wellbore tool of claim 1, further comprising:
an optical detector configured to detect the laser pulse.

5. A wellbore tool comprising:
a photoacoustic system comprising:
a laser system that is configured to generate a laser pulse,
an interface disposed between a fluid sample and the laser system, wherein the interface is configured such that the laser pulse enters the interface, and
an acoustic detector configured to receive an acoustic pulse that is generated in response to absorption of the laser pulse;
an optical detector configured to detect the laser pulse; and
a processing system configured to (i) receive a first electric signal from the acoustic detector representative of the acoustic pulse, (ii) receive a second electric signal from the optical detector representative of the laser pulse, and (iii) determine a speed of sound in the fluid sample using the first electric signal and the second electric signal.

6. The wellbore tool of claim 5, wherein the processing system is further configured to (i) identify a first time corresponding to a peak amplitude of the first electric signal from the acoustic detector, (ii) identify a second time corresponding to a peak amplitude of the electric signal from the optical detector, and (iii) determine a time difference between the first time and the second time.

7. The wellbore tool of claim 6, wherein the processing system is further configured to determine the speed of sound in the fluid sample using the time difference and a distance between the interface and the acoustic detector.

8. The wellbore tool of claim 1, wherein the interface is disposed along a flow line of the wellbore tool, the fluid sample is disposed within the flow line, and the acoustic detector is disposed along the flow line of the wellbore tool.

9. The wellbore tool of claim 1, wherein the laser system comprises a laser cavity with a monolithic body having a first end and a second end, the monolithic body comprising a first reflector disposed on the first end, a second reflector disposed on the second end, a solid state gain medium and a Q-switch, wherein the solid state gain medium and the Q-switch are disposed between the first reflector and the second reflector of the monolithic cavity.

10. The wellbore tool of claim 9, further comprising a pump source, wherein the pump source is configured to cause a population inversion in the solid state gain medium to cause the monolithic body to generate pulses of laser light.

11. The wellbore tool of claim 1, wherein the laser system comprises:
a pump laser configured to generate a pulse of pump laser light; and
an optical parametric oscillator configured to generate the laser pulse, wherein the wavelength of the laser pulse depends on a wavelength of the pulse of pump laser light and a control signal applied to a nonlinear crystal of the optical parametric oscillator.

12. A method for analyzing a fluid sample, the method comprising:
positioning a photoacoustic system within a wellbore, wherein the photoacoustic system comprises a laser system and an acoustic detector;
using the laser system to apply a laser pulse to an interface disposed between the fluid sample and the laser system, wherein the interface is comprised of an absorbing medium that absorbs the laser pulse such that an acoustic pulse is generated by the absorbing medium in response to the absorption;
using the acoustic detector to detect the acoustic pulse that is generated by the absorption of the laser pulse; and
determining a speed of sound in the fluid sample using the detected acoustic pulse.

13. The method of claim 12, wherein the fluid sample is an absorbing medium that generates the acoustic pulse.

14. The method of claim 12, further comprising:
determining compressibility of the fluid sample using the speed of sound.

15. The method of claim 12, wherein the photoacoustic system comprises an optical detector configured to detect the laser pulse.

16. A method for analyzing a fluid sample, the method comprising:
positioning a photoacoustic system within a wellbore, wherein the photoacoustic system comprises a laser system, an acoustic detector, and an optical detector;
using the laser system to apply a laser pulse to an interface disposed between the fluid sample and the laser system, wherein the optical detector is configured to detect the laser pulse;
using the acoustic detector to detect an acoustic pulse generated by absorption of the laser pulse;
determining a speed of sound in the fluid sample using the detected acoustic pulse;
receiving a first electric signal from the acoustic detector representative of the acoustic pulse;
receiving a second electric signal from the optical detector representative of the laser pulse; and
determining the speed of sound in the fluid sample using the first electric signal and the second electric signal.

17. The method of claim 16, further comprising:
identifying a first time corresponding to a peak amplitude of the first electric signal from the acoustic detector;
identifying a second time corresponding to a peak amplitude of the electric signal from the optical detector; and
determining a time difference between the first time and the second time.

* * * * *